United States Patent [19]

Hiratani

[11] Patent Number: 4,609,546

[45] Date of Patent: Sep. 2, 1986

[54] LONG-ACTING COMPOSITION

[75] Inventor: Hajime Hiratani, Sennan, Japan

[73] Assignee: Japan Chemical Research Co., Ltd., Kobe, Japan

[21] Appl. No.: 507,154

[22] Filed: Jun. 23, 1983

[30] Foreign Application Priority Data

Jun. 24, 1982 [JP] Japan ................. 57-108851
Sep. 27, 1982 [JP] Japan ................. 57-169160

[51] Int. Cl.$^4$ .................. A61K 31/745; A61K 39/00; C07K 15/00
[52] U.S. Cl. ........................ 424/83; 424/85; 424/88; 514/2; 530/815; 530/399; 530/351
[58] Field of Search ............... 424/85, 177, 88, 78, 424/83; 260/112 R; 514/2

[56] References Cited

U.S. PATENT DOCUMENTS 4,100,271 7/1978 Krezanoski ................. 424/78
4,179,337 12/1979 Davis et al. ................. 424/78
4,261,973 4/1981 Lee et al. ................... 424/78

*Primary Examiner*—Blondel Hazel
*Attorney, Agent, or Firm*—Burgess, Ryan & Wayne

[57] ABSTRACT

A composition wherein a physiologically active polypeptide or a glycoprotein of human origin, for instance, urokinase, kallikrein or leukocyte interferon, is coupled to a polyoxyethylene-polyoxypropylene copolymer. The composition is effective in the human body for a prolonged period of time.

15 Claims, No Drawings

LONG-ACTING COMPOSITION

This invention relates to a long-active composition which is effective in the human body for a prolonged period of time. More particularly, this invention relates to a long-active composition wherein a physiologically active polypeptide or glycoprotein of human origin is coupled to a polyoxyethylene-polyoxypropylene copolymer.

Physiologically active substances, such as a variety of hormones and enzymes, when administered to living bodies, generally undergo decomposition by various proteases in said living bodies in a short time or immediate inhibition by various inhibitors, so that their effects can last only for a short period of time.

Accordingly, when they are considered as pharmaceuticals, there have been many cases where the expected effects cannot be produced.

Under these circumstances, the present inventors conducted intensive research in search of the possibility of rendering lasting physiological activity in living bodies so that their effects can be ensured to an increased extent and their doses can be reduced. As a result, it has been found that the above objects can be accomplished by coupling physiologically active substances to polyoxyethylene-polyoxypropylene copolymers (hereinafter briefly referred to as "copolymers").

The present invention thus provides long-acting compositions comprising human-derived physiologically active polypeptides or glycoproteins coupled to polyoxyethylene-polyoxypropylene copolymers.

In another aspect thereof, the present invention provides a method of rendering the above-mentioned polypeptides or glycoproteins long-acting by coupling them to the above-mentioned copolymers.

Polyoxyethylene-polyoxypropylene copolymers are available on the market. About 33 species are in main use; they have a molecular weight of 1,000 to 14,000 with varied polyoxyethylene-to-polyoxypropylene ratios, say 4:16, 196:67 or 256:54. However, products obtained by coupling physiologically active substances to those copolymers which have a molecular weight exceeding 10,000 have undesirably decreased activity due to their active groups being wrapped up in or concealed by the copolymer molecules. Such products are undesirable also because they remain in living bodies for an excessively long period and possibly produce side effects.

Accordingly, in accordance with the present invention, only those copolymers that have a molecular weight of about 1,000 to about 10,000 are used. The copolymers have hydroxyl groups at both the ends thereof. The hydrogen atom of one of the hydroxyl groups may be substituted by an alkyl or acyl group. Preferred examples of the alkyl group are methyl and ethyl. Acetyl and propionyl are examples of the acyl group. Substitution by these groups can be performed by known methods.

In practicing the present invention, a polypeptide or glycoprotein of human origin, namely extracted from human urine, placenta or blood components or derived from human blood components or produced by tissue culture of human cells, is used.

Examples of the polypeptide or glycoprotein are human menopausal gonadotropin (HMG), human growth hormone (HGH), epidermal growth factor (EGF), nerve growth factor (NGF), colony formation stimulating factor (CSF), urokinase (UK), plasminogen (PLG), kallikrein, interferon $\alpha$, interferon $\beta$, interferon $\gamma$, interleukin 1, interleukin 2, urinary tripsin inhibitor, urinary thiol protease inhibitor, placental arylsulfatase, urinary lysozyme and urinary asparaginase.

In accordance with the present invention, the above-mentioned copolymers are coupled to such physiologically active polypeptides or glycoproteins. The coupling is effected by means of a coupling agent capable of linking the terminal hydroxyl group of the copolymers with the amino group of the active substances. The coupling agent contains at least one functional group capable of reacting with the hydroxyl group and at least one functional group capable of reacting with the amino group, and includes 2,4,6-trichloro-s-triazine, dibromosuccinic anhydride and maleic anhydride, among others.

Thus, for instance, the copolymers are reacted with 2,4,6-trichloro-s-triazine in the presence of an alkali, and the resulting reactive copolymer derivatives are reacted with the above-mentioned active substances, whereby the active substances are coupled to at least one copolymer molecule through the N-terminal primary amino group and/or the $\epsilon$-amino group or groups in a lysine residue or residues.

The above coupling reaction can be performed by the known methods, the reaction conditions being selected based on the reactivity of each of the terminal hydroxyl groups of the copolymers, the amino group of the active substances, and the coupling agent.

The compositions according to the present invention can produce the effects of the active substances in living bodies for a significantly prolonged period of time; the duration of activity can be prolonged 10 to 20 times, for instance.

Moreover, the copolymer-physiologically active substance coupling products are rather inert to proteases in living bodies and furthermore are not susceptible to various inhibitors in the blood, and therefore said products show marked improvements in development and persistence of activity.

The compositions according to the present invention are administered either orally or parenterally depending on the kind of physiologically active substances. Parenteral administration may be by intravenous, intramuscular or subcutaneous injection.

The dose of the compositions is proportional to the dose known for the physiologically active substances concerned. However, the compositions according to the present invention tend to have a somewhat decreased activity per unit weight as compared with the starting active substances and therefore it is desirable to increase the single dose thereof accordingly. Nevertheless, since they are markedly improved in the duration of effects, as mentioned above, the compositions may be administered every several days or at longer intervals where the corresponding active substances themselves would be administered daily.

The following examples illustrate the present invention in more detail.

EXAMPLE 1

2,4,6-Trichloro-s-triazine (cyanuric chloride) (5.5 g, 30 millimoles) was added to 400 ml of anhydrous benzene containing 10 g of anhydrous sodium carbonate, followed by addition of 50 g (10 millimoles) of methoxy-polyoxyethylene-polyoxypropylene glycol (average molecular weight 5,000, monomethylation product derived from Pluronic F-38 (Asahi Denka Kogyo K.K.), E.O.:P.O.:E.O.=46:16:46). The mixture was stirred at room temperature overnight.

The insoluble matter was filtered off, 5 volumes of petroleum ether was added to the filtrate and the resulting precipitate, activated copolymer, was collected by filtration. Two more redissolution-reprecipitation procedures with benzene and petroleum ether gave 51.5 g of the desired activated copolymer.

Purified urokinase (3 million units) was dissolved in 30 ml of 0.1 M phosphate buffer (pH 7.0) at 4° C. To the solution was added 600 mg of the above activated copolymer, and the mixture was stirred at 4° C. with stirring for 3 hours.

Then, the reaction was terminated by adjusting the pH to not more than 5.0. The unreacted activated copolymer was removed by gel filtration using Sephadex G-100 equilibrated with 0.1 M phosphate buffer (pH 5.0).

The thus-obtained modified urokinase had an average molecular weight of 150,000 and retained 40% (fibrin plate method) or 70% (fluorogenic substrate method) of the original activity.

The half lives in the blood of the unmodified urokinase and the modified urokinase as determined in rabbits were 5 minutes and 120 minutes, respectively, the half life ratio thus being as high as 24. The half life determination was conducted in the following manner.

The unmodified or modified urokinase (50,000 units/kg) was administered to rabbits weighing about 2.0 kg into the auricular vein on the side oposite to the ear where blood sampling was conducted at timed intervals.

Blood sampling was performed by connecting a syringe with an indwelling needle in the auricular vein. Ten to thirty minutes before urokinase administration, heparin sodium was intravenously administered in a dose of 1,000 units/kg.

Before administration of the sample, immediately after administration, and 2 minutes, 5 minutes, 10 minutes, 20 minutes, 30 minutes, 40 minutes, 60 minutes, 120 minutes and 240 minutes after administration, 2 ml of blood was collected from each animal and immediately centrifuged (3,000 rpm, 5 minutes), and the plasma was assayed for urokinase activity. The above-mentioned results were obtained in that manner.

The fibrin plate method used in this example for urokinase activity determination was performed as described by P. L. Walton in Clin. Chim. Acta, 13 (5), 6806-84 (1966).

The fluorogenic substrate method was performed as described by T. Morita et al. in J. Biochem., (82, 1495 (1977).

EXAMPLE 2

100,000 units of human urinary kallikrein purified almost to absolute purity was dissolved in 50 ml of 0.1 M phosphate buffer (pH 7.0) at 4° C. Ethoxy-polyoxyethylenepolyoxypropylene glycol (average molecular weight 3,400, E.O.:P.O.:E.O.=19:30:19, Asahi Denka Kogyo's Pluronic P-65) was activated in the same manner as in Example 1. The activated copolymer (0.7 g) was added to the above solution, and the mixture was stirred at 4° C. for 3 hours.

Then, the reaction was terminated by adjusting the pH to not more than 5.0, and the unreacted activated copolymer was removed by dialyzing the reaction mixture at 4° C. overnight against 0.1 M phosphate buffer (pH 5.0).

The thus-obtained modified kallikrein had an average molecular weight of 100,000 and retained 50% (hypotension method using dogs) or 80% (fluorogenic substrate method using Pro-Phe-Arg-MCA) of the original activity.

The half lives of the unmodified kallikrein and the modified kallikrein were determined in rabbits by collecting blood samples in the same manner as in Example 1. They were 7 minutes and 110 minutes, respectively, and the ratio therebetween amounted to 15.

The hypotension method using dogs as used in this example for the assay of kallikrein was performed as described in J. Biochem., 58, 201 (1965).

The fluorogenic substrate method was performed as described in J. Biochem., 82, 1495 (1977).

EXAMPLE 3

100 million units of human leukocyte interferon (specific activity $2 \times 10^7$ units/mg protein) was dissolved in 22 ml of 0.1 M phosphate buffer (pH 7.0) at 4° C., then 220 mg of the same activated copolymer as used in Example 1 was added, and the mixture was stirred at 4° C. for 3 hours. Then, the reaction was terminated by adjusting the pH to not more than 5.0, and the unreacted activated copolymer was removed by subjecting the reaction mixture to dialysis against 0.1 M phosphate buffer (pH 5.0) at 4° C. overnight. The thus-obtained modified interferon α retained 40% of the activity before modification. The cells used in the activity determination were FL-cells [human amniotic cells (Fogh & Lund strain)]. VSV (vesicular stomatitis virus) was used as the challenging virus. The CPE (cytopathogenic effect) manifested by the microplate method was judged by the dye uptake method [N. B. Finter, J. General Virology, 5, 419 (1969)] using phenol red. The half lives in rabbit blood of the unmodified interferon α and the modified interferon α as determined with blood samples collected in the same manner as in Example 1 were 5 minutes and 80 minutes, respectively, revealing a 16 times prolonged half life of the modified one.

I claim:

1. A long-acting composition which comprises a physiologically active polypeptide or glycoprotein of human origin coupled to a polyoxyethylene-polyoxypropylene copolymer having a molecular weight between about 1,000 and about 10,000 by means of a coupling agent capable of linking the terminal hydroxyl group of said copolymer with the amino group of said active substance.

2. A composition according to claim 1 wherein the physiologically active polypeptide or glycoprotein of human origin is human menopausal gonadotropin, human growth hormone, epidermal growth factor, nerve growth factor, colony formation stimulating factor, urokinase, plasminogen (PLG), kallikrein, interferon α, interferonβ, interferonγ, interleukin 1, interleukin 2. urinary trypsin inhibitor, urinary thiol protease inhibitor, placental arylsulfatase, urinary lysozyme or urinary asparaginase.

3. A composition according to claim 1 wherein the copolymer has a molecular weight of between about 1,000 and about 10,000 having at both ends thereof hydroxyl groups which may be substituted by an alkyl or acyl group.

4. A composition according to claim 1 wherein the copolymer has a polyoxyethylene- polyoxypropylene ratio from 4:16 to 256:54.

5. A composition according to claim 1 wherein the copolymer is a monomethylation product of a polyoxyethylene-polyoxypropylene copolymer having an ethylene oxide: propylene oxide: ethylene oxide ratio of 46:16:46 and having an average molecular weight of 5,000.

6. A composition according to claim 1 wherein the copolymer is an ethyoxy-polyoxyethylene-polyoxypropylene glycol having an average molecular weight of 3,400 and an ethylene oxide:proplyene oxide:ethylene oxide ratio of 15:30:19.

7. A composition according to claim 1 wherein the coupling agent contains at least one functional group capable of reacting with a hydroxyl group and at least one functional group capable of reacting with an amino group.

8. A composition according to claim 1 wherein the coupling agent is 2,4,6-trichloro-s-triazine, dibromosuccinic anhydride or maleic anhydride.

9. A long-acting composition which comprises a physiologically active polypeptide or glycoprotein of human origin selected from the group of human epidermal growth factor, urokinase, kallikrein and leukocyte interferon, coupled to a polyoxyethylene-polyoxypropylene copolymer having a molecular weight between about 1,000 and about 10,000, by means of a coupling agent capable of linking the terminal hydroxyl group of said copolymer with the amino group of said active substance.

10. A pharmaceutical composition useful for prolonging the effect of a physiologically active polypeptide or glycoprotein of human origin, comprised of a pharmaceutically effective prolonging amount of the long-acting composition of claim 1 and a pharmaceutically acceptable carrier.

11. A pharmaceutical composition useful for prolonging the effect of a physiologically active polypeptide or glycoprotein of human origin, comprised of a pharmaceutically effective prolonging amount of the long-acting composition of claim 2 and a pharmaceutically acceptable carrier.

12. A pharmaceutical composition useful for prolonging the effect of a physiologically active polypeptide or glycoprotein of human origin, comprised of a pharmaceutically effective prolonging amount of the long-acting composition of claim 9 and a pharmaceutically acceptable carrier.

13. A method for prolonging the effect of a physiologically active substance in the human body which comprises administering to said human body a pharmaceutically effective amount of the pharmaceutical composition of claim 10 which contains said physiologically active substance.

14. A method for prolonging the effect of a physiologically active substance in the human body which comprises administering to said human body a pharmaceutically effective amount of the pharmaceutical composition of claim 11 which contains said physiologically active substance.

15. A method for prolonging the effect of a physiologically active substance in the human body which comprises administering to said human body a pharmaceutically effective amount of the pharmaceutical composition of claim 12 which contains said physiologically active substance.

* * * * *